United States Patent [19]

Shealy

[11] Patent Number: 5,124,083

[45] Date of Patent: Jun. 23, 1992

[54] 3-SUBSTITUTED AND 3,3-DISUBSTITUTED 4-OXORETINOIC ACIDS AND THEIR ESTERS

[75] Inventor: Y. Fulmer Shealy, Birmingham, Ala.

[73] Assignee: Southern Research Institute, Birmingham, Ala.

[21] Appl. No.: 575,082

[22] Filed: Aug. 30, 1990

[51] Int. Cl.⁵ .............................................. C11C 3/02
[52] U.S. Cl. ................................. 514/529; 568/824; 514/545; 514/547; 514/549; 514/725; 554/116; 554/118; 560/51; 560/54; 560/126
[58] Field of Search .................... 260/410.9; 568/824; 514/724

[56] References Cited

PUBLICATIONS

Shealy, *Preventive Medicine*, vol. 18, pp. 624-645, 1989.
Roberts and Frolik, *Federation Proceedings*, vol. 38, No. 11, pp. 2524-2527, 1979.
Roberts et al, *Archives of Biochemistry and Biophysics*, vol. 199, No. 2, pp. 374-383, 1980.
Frolik, *The Retinoids*, vol. 2, edited by M. B. Sporn, A. B. Roberts and D. S. Goodman, Academic Press, Inc. Orlando, Fla., 1984, pp. 177-208.

*Primary Examiner*—Jose G. Dees
*Assistant Examiner*—Deborah D. Carr
*Attorney, Agent, or Firm*—Roylance, Abrams, Berdo & Goodman

[57] ABSTRACT

There are disclosed 3-substituted and 3,3-disubstituted all-trans-4-oxoretinoic acids and 3-substituted and 3,3-disubstituted 13-cis-4-oxoretinoic acids and their lower alkyl esters.

24 Claims, No Drawings

3-SUBSTITUTED AND 3,3-DISUBSTITUTED 4-OXORETINOIC ACIDS AND THEIR ESTERS

BACKGROUND OF THE INVENTION

This invention relates to 3-substituted-4-oxoretinoic acids and 3,3-disubstituted-4-oxoretionoic acids and their esters.

In the discussion which follows, reference will be made to structures having the following formulas and sets of values:

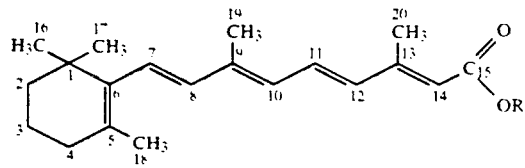

Structure I
a R = H; Retinoic Acid (RA)
b R = CH$_3$; Methyl Retinoate (Methyl RA)

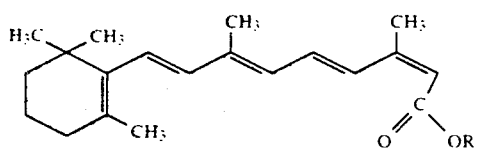

Structure II
a R = H; 13-Cis-retinoic Acid (13-Cis-RA)
b R = CH$_3$; Methyl 13-Cis-retinoate (Methyl 13-Cis-RA)

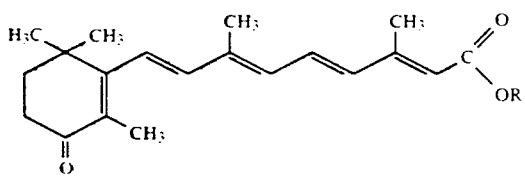

Structure III
a R = H; i.e., 4-Oxoretinoic Acid (4-Oxo-RA)
b R = Alkyl or Aryl groups, e.g.,
  R = methyl (Methyl 4-oxoretinoate of methyl 4-oxo-RA)

It is known that administration of certain retinoids (compounds of the vitamin A group and their derivatives and analogues) may prevent or reduce carcinogen-induced neoplasia in epithelial tissues of animals, and that all-trans-retinoic acid (Structure Ia), 13-cis-retinoic acid (Structure IIa), and some of their derivatives and analogues exert a prophylactic effect on the development of pre-neoplastic and malignant epithelial lesions and may have a therapeutic effect on established cancers. Some examples of these effects in vivo are summarized by Moon et al. [Carcinogenesis, Vol. 3, No. 12, pages 1469-1472 (1982); Cancer Research (Supplement), Vol. 43, pages 2469s-2475s (1983); The Retinoids, Vol. 2, edited by M. B. Sporn, A. B. Roberts and D. S. Goodman, Academic Press, Inc., Orlando, Florida, 1984, pages 327-371]. Moreover, certain retinoids have demonstrated efficacy in the treatment of several human pre-malignancies and malignancies; see, for example, S. M. Lippman, J. F. Kessler, and F. L. Meyskens, Jr., Cancer Treatment Reports, Vol. 71, No. 5, pages 493-515, 1984. Furthermore, retinoids that induce differentiation of neoplastic cells or that potentiate immune responses may be useful in combination with cytotoxic anticancer drugs in the treatment of human cancers (e.g., Lotan and Nicholson, Biochemical Pharmacology, Vol. 37, No. 2, pages 149-154, 1988). Bioassays of new retinoids in organ-culture or cell-culture systems, in biochemical processes, and in animal models identify compounds that may be useful for preventing or treating pre-malignant, malignant, or other human conditions (e.g., Sporn and Roberts, The Retinoids, Vol. 1, edited by M. B. Sporn, A. B. Roberts and D. S. Goodman, Academic Press, Inc., Orlando, Fla., 1984, pages 235-279].

It has been shown that all-trans-4-oxoretinoic acid (Structure IIIa), also known as all-trans-4-ketoretinoic acid, is one of the metabolites of all-trans-retinoic acid (Ia) [Roberts and Frolik, Federation Proceedings, Vol. 38, No. 11, pages 2524-2527, 1979; Roberts et al., Archives of Biochemistry and Biophysics, Vol. 199, No. 2, pages 374-383, 1980; Frolik, The Retinoids Vol. 2, edited by M. B. Sporn, A. B. Roberts, and D. S. Goodman, Academic Press, Inc., Orlando, Fla. 1984, pages 177-208]. It has been postulated that 4-oxo-RA (IIIa) is a deactivation product of RA and a stage in the elimination of RA from the body [Roberts and Frolik, Roberts et al., Frolik; three citations above].

SUMMARY OF THE INVENTION

In the description which follows, references will be made to structures and to compound numbers identified by the following formulas and sets of values:

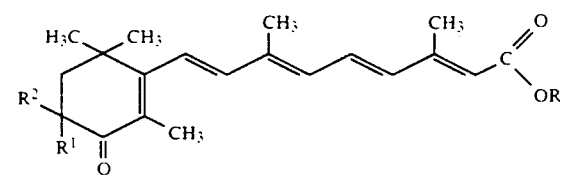

Structure IV

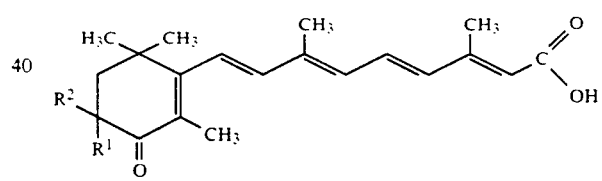

Structure V

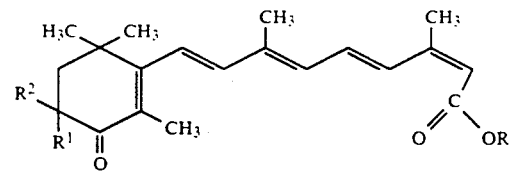

Structure VI

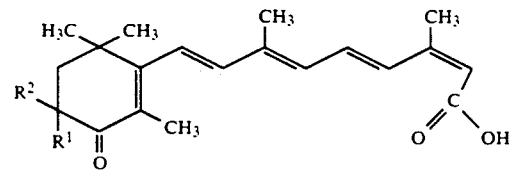

Structure VII wherein R is a lower alkyl group or an aryl group, and R$^1$ and R$^2$ are the same or different substituents selected from the group consisting of hydrogen, an alkyl group, an aralkyl group, an alkenyl group, an aralkenyl or aralkynyl group, an alkynyl group, and a carboxyalkyl group, provided that $R^1$ and $R^2$ are not both hydrogen. Preferably, R is a lower alkyl group containing from 1-6 carbon atoms, and $R^1$ and/or $R^2$ are hydrogen, an alkyl group containing from 1-10 carbon atoms, an aralkyl group containing from 7-10 carbon atoms, an alkenyl group containing from 3-7 carbon atoms, an aralkenyl or aralkynyl group containing from 9-12 carbon atoms, an alkynyl group containing from 3-7 carbon atoms, and a carboxyalkyl group containing from 2-10 carbon atoms, provided that $R^1$ and $R^2$ are not both hydrogen.

This invention provides 3-substituted and 3,3-disubstituted all-trans-4-oxoretinoic acids and 3-substituted and 3,3-disubstituted 13-cis-4-oxoretinoic acids and their lower alkyl esters. Structures IV and V represent such derivatives of all-trans-4-oxoretinoic acids and their esters, respectively. Structures VI and VII represent such derivatives of 13-cis-4-oxoretinoic acids and esters, respectively.

These compounds are useful for the prevention of cancer, for the treatment of pre-malignant conditions, or for the treatment, alone or in combination with other agents, of established cancers by administering to an individual in need of such treatment a therapeutically effective amount of such compounds.

Although 4-oxo-RA has been postulated to be a deactivation and an elimination product of RA, the compounds of this invention might have different pharmacokinetic and elimination properties and be superior in biological activities and toxicological effects.

DETAILED DESCRIPTION OF THE INVENTION

The 3-substituted-4-oxoretinoic acid esters (Structure IV with $R^1$=a substituent and $R^2$=H) of this invention are prepared from an alkyl or aryl ester (Structure IIIb) of 4-oxoretinoic acid, an alkylating agent, and a strong base. The alkylating agent may be an organic halide or an organic sulfonate in which the organic group is an alkyl, an alkenyl, or an alkynyl group or such groups that also bear an aryl group or a polar group, such as an ester group. The basic catalyst may be an alkali metal derivative such as lithium hexamethyldisilazide, lithium diisopropylamide, sodium hydride, or other strong anhydrous bases. Typically, the reaction is allowed to proceed at low temperatures. The desired product (Structure IV) is isolated and purified by chromatographic methods and recrystallization. Two substituents may be introduced at position 3 (Structure IV when both $R^1$ and $R^2$ are the substituents stated above). Two substituents may be introduced by beginning with a 3-substituted-4-oxoretinoic acid ester (Structure IV, $R^1$=a substituent and $R^2$=hydrogen) and applying methods and procedures similar to those employed for the introduction of the first substituent at position 3. Alternatively, such 3,3-disubstituted-4-oxoretinoic acid esters may be obtained in one operational step by increasing the quantities of the alkylating agent and the base.

3-Substituted and 3,3-disubstituted 13-cis-4-oxoretinoic acid esters (Structure VI) may be prepared by similar methods and procedures by beginning with an ester of 13-cis-4-oxoretinoic acid (Structure VI with R =an alkyl or aryl group and $R^1=R^2$=hydrogen).

The corresponding 3-substituted and 3,3-disubstituted 4-oxoretinoic acids (Structure V) and the 3-substituted and 3,3-disubstituted 13-cis-4-oxoretinoic acids (Structure VII) may be prepared by hydrolyzing the esters (Structure IV or Structure VI, respectively) by conventional methods.

Although it has been postulated, as stated in "Background of the Invention", that 4-oxoretinoic acid is an elimination metabolite of retinoic acid, analogues that have substituents at position 3 (Structures IV-VII) will have different pharmacokinetic and elimination properties, and they might be superior in biological activities and be less toxic. Evidence of the utility of retinoids represented by Structures IV-VII is illustrated by bioassays of representatives of these structures for the prevention of cancer (cancer chemopreventive activity).

Induction of differentiation of cancer cells is a potential mode of cancer chemoprevention. It has been reported that RA, 13-cis-RA, and some other retinoids are highly active inducers of differentiation of certain neoplastic cells to terminally differentiated cells. Activity varies with the structure of the retinoid, RA being one of the most active retinoids. Strickland and co-workers showed that a mouse embryonal carcinoma cell line, F9 cells, may be induced by certain retinoids to differentiate into parietal endoderm (S. Strickland and V. Mahdavi, *Cell*, Vol. 15, pages 393-403, 1978; S. Strickland and M. J. Sawey, *Journal of Dev. Biol.*, Vol. 78, pages 76-85, 1980). Elevated release of plasminogen activator by F9 cells in the presence of retinoids is a marker for differentiation. Induction of differentiation of F9 cells by several of the retinoids of this invention was evaluated, and the results are summarized in Table I (Example 24) as values of $ED_{50}$. All of the tested 4-oxoretionoic acid analogues induce differentiation at low concentrations ($ED_{50} = 10^{31\ 9} - 10^{-10}$ molar) and, therefore, are very effective inducers of differentiation of mouse F9 embryonal carcinoma cells. The most active analogues have a free carboxyl group. Under the conditions of this assay, ester derivatives might be hydrolyzed partially to the carboxylic acids.

Some of these 4-oxoretinoic acid analogues were evaluated in the hamster-trachea organ-culture assay described in Clamon et al., *Nature*, Vol. 250, pages 64-66, 1974; Sporn et al., *Nature*, Vol. 263, pages 110-113, 1976; and Newton et al., *Cancer Res.*, Vol. 40, pages 3413-3425, 1980. This bioassay is specific for retinoids and assesses the capacity of retinoids to reverse keratinization in vitamin A-deficient hamster trachea in culture. Therefore, it is a measure of the capacity of a retinoid to control differentiation of epithelial cells, and "it is believed to have significant predictive value for the potential use of a new retinoid for prevention of epithelial cancer" (Newton et al., *Cancer Res.*, Vol. 40, pages 3413-3425, 1980). The results of assays of some of these 4-oxoretinoic acid analogues in the hamster-trachea system are summarized in Table II. (See Example 25). Also, data obtained by Newton *et al.*, (*Cancer Res.*, Vol. 40, pages 3413-3425, 1980) in assays of six all-trans or 13-cis retinamides are included in Table II for comparison. These six retinamides suppress bladder carcinogenesis in vivo, and 4-HPR and 13-cis-4-HPR suppress mammary carcinogenesis in rats (Moon et al., *Cancer Research* (Supplement), Vol. 43, pages 2469s-2475s, 1983). The data in Table II show that 3-substituted-4-oxoretinoic acid derivatives and 3,3-disubstituted-4-oxoretinoic acid derivatives are active in the hamster-trachea organ-culture assay. Furthermore, the activity exerted by these types of structure (e.g., Examples 11 and 20) is comparable to the activity in this assay of the retinamides, listed in the lower part of Table II, that have cancer chemopreventive activity in vivo.

A bioassay in vivo for activity in the prevention of carcinogen-induced cancer is based on the reduction by a retinoid of the amount of ornithine decarboxylase (ODC) induced in mouse skin by the tumor promoter 12-O-tetradecanoylphorbol 13-acetate (TPA). Verma et al. (*Cancer Research*, Vol. 38, pages 793-801, 1978), reported that "application of the potent tumor-promoting agent 12-O-tetradecanoylphorbol 13-acetate (TPA) to mouse skin leads to a rapid and transient induction of epidermal ornithine decarboxylase activity". They state, further, that "inhibition of this enzyme activity by retinoids may be a simple and rapid in vivo test for assessing the potential prophylactic activity of new synthetic retinoids". The results of the ODC assay of 4-oxoretinoids of this invention are summarized in Table III (Example 26). All of the tested 4-oxoretinoid analogues reduced TPA-induced ODC activity. The compounds of Examples 2-4, 8, 11, 17, 18, and 20-23 reduced ODC activity to 22-47% of the ODC activity in the control mice and are, therefore, very active in this assay for cancer chemopreventive activity.

Application of the carcinogen DMBA to mouse skin followed by application of the tumor promoter TPA causes the formation of papillomas. Certain retinoids applied to the same area of mouse skin reduce or prevent papilloma formation (e.g. H. Mayer, W. Bollag, R. Hanni, and R. Ruegg, *Experientia*, Vol 34, pages 1105-1119, 1978; R. K. Boutwell and A. K. Verma, *Pure and Applied Chemistry*, Vol. 51, pages 857-866, 1979). The antipapilloma assay is a direct test of the capability of a retinoid to prevent tumor formation in vivo. It has been used to select retinoids for clinical development. The results of assays of several of the 4-oxoretinoids of this invention are summarized in Table IV (Example 27). The tested retinoids reduced papilloma formation to 27-83% of papilloma formation in untreated control mice. In these tests, methyl 3-methyl-4-oxoretinoate (Example 2), methyl 3-propynyl-4-oxoretinoate (Example 8), methyl 3,3-dimethyl-4-oxoretinoate (Example 11), 3-methyl-4-oxoretinoic acid (Example 17), 3-cinnamyl-4-oxoretinoic acid (Example 22), and 3,3-dimethyl-4-oxoretinoic acid (Example 23) were the most active of the tested 4-oxoretinoids. The number of papillomas in mice treated with either of these six retinoids was 27-40% of the number of papillomas on untreated mice; or, differently expressed, papilloma formation was reduced by 60-73%.

In the examples which follow, all operations involved in the preparation, isolation, purification, and transfer of retinoids were performed in an atmosphere, or under a current, of nitrogen or argon. All such operations were also performed in dim light or photographic dark room light and, insofar as possible, with containers wrapped with aluminum foil or with black cloths. All retinoids were stored in an atmosphere of argon or nitrogen in hermetically sealed containers at $-20°$ C. or $-80°$ C.

Melting temperatures were determined in capillary tubes heated in a Mel-Temp apparatus. Ultraviolet spectra (UV) were determined with ethanol solutions and were recorded with a Perkin-Elmer UV-Visible-NIR spectrophotometer; maxima are given in nanometers. Mass spectral (MS) data were taken from low-resolution, electron-impact spectra, unless stated otherwise, determined at 70 eV with a Varian/MAT Model 311A spectrometer. Data taken from fast-atom-bombardment are designated FAB MS. M=molecular ion; some of the other peaks are identified as probable fragments, e.g., M minus a fragment. Proton nuclear magnetic resonance spectra ($^1$H-NMR) were determined at 300.64 MHz with a Nicolet 300 NB NMR spectrometer; the solvent was CDCl$_3$ unless stated otherwise. Chemical shifts ($\delta$) are given in parts per million downfield from tetramethylsilane, the internal standard. Assignments of chemical shifts are designated by the position numbers shown on Structure I. Multiplicity of the chemical shifts and the position numbers are given parenthetically with each chemical shift; s=singlet, d=doublet, t=triplet, q=quartet, m=multiplet, dd=doublet of doublets, a=axial, e=equatorial. High-pressure liquid chromatography (HPLC) was performed with Waters Associates components systems and a Hewlett-Packard Model 3380-S integrator or with a Hewlett-Packard Model 1084B system. HPLC was performed on columns packed with octadecylsilylated silica (Spherisorb ODS), 5$\mu$particle size; unless indicated otherwise, the eluting solvent was 85:15 acetonitrile-1% aqueous ammonium acetate, isocratic, 1 mL/minute flow rate; and elution was monitored by UV absorption at 340 nm.

In the following examples, all alkylations were carried out in oven-dried glassware and under an argon atmosphere. A Firestone valve was employed to maintain a positive argon pressure when reactants were being added to the cold reaction solution.

EXAMPLE 1

General Procedure for the Preparation Of Methyl 3-Substituted-4-oxoretinoates (Structures IV and VI)

A solution of methyl 4-oxoretinoate (compound IIIb, R=methyl) in anhydrous tetrahydrofuran (THF) (2.5-5 mL/mmol) was added from an addition funnel during 5-10 minutes to a cold solution, maintained at $-78°$ C., of lithium hexamethyldisilazide (1-1.3 equiv.) in anhydrous THF. The solution of lithium hexamethyldisilazide had been prepared by diluting a 1 molar THF solution of the base with 1-3 mL of anhydrous THF per mmol of the base. The solution of compound IIIb (R=methyl) and the base was stirred at $-78°$ C. for 30 minutes, and the alkylating agent (2 equiv.) was added. The reaction mixture was stirred for 30 minutes at $-78°$ C., allowed to warm slowly to room temperature, and then, typically, was stirred overnight. Most of the THF and the excess alkylating agent (if sufficiently volatile) were evaporated under reduced pressure, a saturated solution of ammonium chloride was added to the residue, and the aqueous mixture was extracted (3x) with ether or ethyl acetate. The ether or ethyl acetate solution was dried (MgSO$_4$), and the organic solvent was evaporated under reduced pressure. The residual crude methyl 3-substituted-4-oxoretinoate was purified by preparative thin layer chromatography (TLC), gravity chromatography, flash chromatography, recrystallization, or sequences of these techniques.

EXAMPLE 2

Methyl 3-Methyl-4-oxoretinoate (Compound IV; R=CH$_3$, R$^1$=CH$_3$, R$^2$=H)

A solution of 17 millimoles of lithium hexamethyldisilazide in THF was prepared from 24 mL of anhydrous THF and 17 mL of a 1 molar solution of the hexamethyldisilazide base in THF, and this solution was chilled to $-78°$ C. A solution of 5.0 g (15.2 mmol) of methyl 4-oxoretinoate dissolved in 48.3 mL of anhydrous THF was added during 10 minutes to the stirred, cold (−78° C.) hexamethyldisilazide solution. After the resulting mixture had been stirred at −78° C. for 30 minutes, methyl iodide (1.86 mL, 30 mmol) was added, the temperature of the reaction mixture was allowed to rise to room temperature, and the mixture was stirred overnight and then concentrated under reduced pressure. A saturated aqueous solution (40 mL) of ammonium chloride was added to the residue, the mixture was extracted twice with 30-mL portions of ethyl acetate, and the ethyl acetate extract was dried by adding magnesium sulfate and alumina and stirring the mixture. The mixture was filtered, the filtrate was concentrated under reduced pressure to a solid (weight 4.69 g), and the residue was triturated with petroleum ether: weight, 4.05 g (77% yield); m.p. 121°–123° C. ; HPLC, 90.5% of compound IV with $R = R^1 = CH_3$, $R^2 = H$. A second portion (306 mg) was obtained by crystallizing the filtrate residue from ether-pentane. The two portions were combined and subjected to chromatography on a column of silica gel. Elution by heptane-ethyl acetate (9:1) was monitored by thin-layer chromatography. Fractions that showed one spot on thin-layer chromatograms were combined and recrystallized from ether-pentane: yield of yellow crystals from the cold solvent, 3.126 g (60%); m.p. 125°–126° C.; MS peaks at m/z 342 (M), 327 (M-CH$_3$), 295 (M-CH$_3$-CH$_3$OH), 283 (M-COOCH$_3$); UV$_{max}$ at 361 nm ($\epsilon$ 53 000), 285 nm ($\epsilon$ 12 300), 231 nm ($\epsilon$ 7900); HPLC, 98.1–99.6% (85:15 acetonitrile-1% aqueous ammonium acetate; $^1$H NMR $\delta$ 1.14 (s, 17e) 1.14 (d, 3-CH$_3$), 1.24 (s, 16a), 1.71 and 1.76 (ABM spin system, 2a and 2e) , 1.85 (s, 18), 2.03 (s, 19), 2.36 (s, 20), 2.56 (m, 3a), 3.72 (s, OCH$_3$), 5.82 (14, unresolved m), 6.25 (d, 10), 6.32 (s, 7), 6.32 (s, 8), 6.35 (d, 12), 6.98 (dd, 11). Analysis. Calculated for C$_{22}$H$_{30}$O$_3$: C, 77.15; H, 8.83. Found: C, 77.22; H, 8.76.

EXAMPLE 3

Methyl 3-Cinnamyl-4-oxoretinoate (Compound IV: $R = CH_3$, $R^1 = C_6H_5CH=CHCH_2-$, $R^2 = H$)

A solution of 3.0 g (9.13 mmol) of methyl 4-oxoretinoate (IIIb) dissolved in 29 mL of anhydrous THF was added to a THF solution of 9.13 mmol of lithium hexamethyldisilazide. The solution of lithium hexamethyldisilazide had been prepared, as described in Example 1, from 14.5 mL of anhydrous THF and 1 molar lithium hexamethyldisilazide in THF and was maintained at −78° C. After the mixture had been stirred for 30 minutes, a solution of 2.70 g (13.7 mmol) of cinnamyl bromide in 3 mL of anhydrous THF was added to the cold, stirred mixture. The temperature of the reaction mixture was allowed to rise slowly to room temperature, and the mixture was stirred overnight. The reaction mixture was processed as described in Example 1, and the ethyl acetate extract was dried with magnesium sulfate and evaporated under reduced pressure to a solid. The crude product was chromatographed on a column of silica gel with gravity elution by heptane-ethyl acetate (9:1). Thin-layer chromatography indicated that the first fraction (1.29 g) contained cinnamyl bromide as well as the desired product named in the title of this example; the second fraction (3.18 g) consisted of the desired product and minor impurities. The first fraction was separated into two fractions by flash chromatography on a column of silica gel with pentane-ethyl acetate (9:1) as the eluting solvent; flash chromatography of the second flash-chromatography fraction, which was contaminated by cinnamyl bromide, was repeated in the same way. The first fractions (0.28 g and 0.33 g) from the two flash chromatography columns were combined with the second fraction (3.18 g) from the gravity column, and the total product, which was free of cinnamyl bromide, was purified further by gravity chromatography on a column of silica gel with elution successively by heptane and by heptane containing 1, 2, 5, or 10% ethyl acetate. Fractions containing almost pure methyl 3-cinnamyl-4-oxoretinoate were combined and concentrated to dryness, and the residue (3.53 g; yield, 87%) was recrystallized from ether-pentane: yield 2.17 g (53%); m.p. 74°–75° C. A polymorphic form was obtained by evaporating the solvent from an ethanol solution of methyl 3-cinnamyl-4-oxoretinoate: m.p. 84°–85° C. ; MS peaks at m/z 444 (M), 429 (M-CH$_3$), 388, 327 (M-cinnamyl group), 117 (cinnamyl group); UV$_{max}$ 362 nm ($\epsilon$ 53 900), 292 nm (sh), 284.5 nm ($\epsilon$ 13 700), 252 nm ($\epsilon$ 23 700); HPLC, 98.2–99.5% (85:15 acetonitrile-1% aqueous ammonium acetate); $^1$H NMR $\delta$ 1.14 (s, 17e), 1.23 (s, 16a), 1.70 and 1.83 (ABM spin system, 2a and 2e), 1.87 (s, 18), 2.03 (s, 19), 2.31 (m, CH$_2$ of cinnamyl group), 2.36 (d, 20), 2.61 (m, 3a), 2.85 (m, CH$_2$ of cinnamyl group), 3.72 (s, OCH$_3$), 5.82 (unresolved m, 14), 6.21 (ABM$_2$ spin system, CH of =CHCH$_2$— of cinnamyl), 6.25 (d, 10), 6.33 (s, 7), 6.33 (s, 8), 6.35 (d, 12), 6.43 (ABM$_2$ spin system, CH of C$_6$H$_5$CH= of cinnamyl), 6.98 (dd, 11), 7.17–7.38 (aromatic CH). Analysis. Calculated for C$_{30}$H$_{36}$O$_3$: C, 81.04; H, 8.16. Found: C, 81.15; H, 8.20.

EXAMPLE 4

Methyl 3-Ethyl-4-oxoretinoate (Compound IV: $R = CH_3$, $R^1 = CH_3CH_2-$, $R^2 = H$)

This compound was prepared from methyl 4-oxoretinoate, lithium hexamethyldisilazide, and ethyl iodide in anhydrous THF according to the general procedure (Example 1). The crude product was purified by preparative TLC (silica gel; developing solvent 8:2 pentane-ethyl acetate) or column chromatography and by recrystallization from ether-pentane or ether-hexane: m.p. 97°–99° C.; MS peaks at m/z 356 (M), 341 (M - CH$_3$), 297 (M-COOCH$_3$); UV$_{max}$ 360 nm ($\epsilon$ 54 000), 284 nm ($\epsilon$ 12 700), 230 ($\epsilon$ 8200); HPLC, 99.7–100% (85:15 acetonitrile-1% ammonium acetate); $^1$H NMR $\delta$ 0.94 (t, CH$_3$ of 3-ethyl), 1.16 (s, 17e), 1.23 (s, 16a), 1.39 (m, CH$_2$ of 3-ethyl), 1.69 and 1.80 (ABM spin system, 2a and 2e), 1.85 (s, 18), 1.97 (m, CH$_2$ of 3-ethyl), 2.03 (s, 19), 2.36 (d, 20), 2.36 (m, 3a), 3.72 (s, OCH$_3$), 5.82 (unresolved m, 14), 6.25 (d, 10), 6.33 (s, 7), 6.33 (s, 8), 6.36 (d, 12), 6.94 (dd, 11). Analysis. Calculated for C$_{22}$H$_{32}$O$_3$: C, 77.17; H, 8.87. Found: C, 77.49; H, 9.04.

EXAMPLE 5

Methyl 3-Isopropyl-4-oxoretinoate (Compound IV; $R = CH_3$, $R^1 = (CH_3)_2CH-$, $R^2 = H$)

Methyl 4-oxo-RA was treated with isopropyl iodide according to the procedure described in Example 1. The crude product was purified by preparative TLC on silica gel (developing solvent, 8:2 hexane-ethyl acetate). A pure specimen of methyl 3-isopropyl-4-oxoretinoate (C$_{24}$H$_{34}$O$_3$) was obtained from the leading band and identified by mass spectral analysis: analytical TLC, 1 spot; MS peaks at m/z 370 (M of C$_{24}$H$_{34}$O$_3$) 355 (M-CH$_3$), 338 (M-CH$_3$OH), 323 (M-CH$_3$-CH$_3$OH).

EXAMPLE 6

Methyl 3-(tertiary-Butyl)-4-Oxoretinoate (Compound IV; R=CH$_3$, R$^1$=(CH$_3$)$_3$C-, R$^2$=H)

Methyl 4-oxoretinoate was treated with tertiary-butyl iodide according to the procedure described in Example 1. Mass spectral analysis of the total crude product showed that it contained the tertiary-butyl derivative (Compound IV; R=CH$_3$, R$^1$=(CH$_3$)$_3$C-, R$^2$=H): MS peaks at m/z 384 (M of C$_{25}$H$_{36}$O$_3$), 369 (384-CH$_3$), 328 (M of methyl 4-oxo-RA), 313 (328-CH$_3$), 281 (328-CH$_3$-CH$_3$OH).

EXAMPLE 7

Methyl 4-Oxo-3-(2-propenyl)retinoate (Compound IV; R=CH$_3$, R$^1$=CH$_2$=CHCH$_2$-, R$^2$=H)

This compound was prepared, according to the general procedure described in Example 1, from methyl 4-oxo-RA and allyl bromide. The crude product was purified by flash chromatography (on silica gel with 9:1 pentane-ethyl acetate as eluting solvent) followed by recrystallization from ether pentane: m.p. 95°-96° C.; HPLC, 99.4-100% (85:15 acetonitrile-1% aqueous ammonium acetate); MS peaks at m/z 368 (M), 353 (M-CH$_3$), 336 (M-CH$_3$OH), 321 (M-CH$_3$-CH$_3$OH); UV$_{max}$ 361 nm ($\epsilon$ 53 500), 285 nm ($\epsilon$ 12 800), 231 nm ($\epsilon$ 8300); $^1$H NMR $\delta$ 1.15 (s, 17e), 1.23 (s, 16a), 1.64 and 1.80 (ABM spin system, 2a and 2e), 1.86 (s, 18), 2.03 (s, 19), 2.10 (m, —CH$_2$CH=CH$_2$), 2.36 (d, 20), 2.52 (m, 3a), 2.74 (m, —CH$_2$CH=CH$_2$), 3.72 (s, OCH$_3$), 5.07 (m, CH$_2$=CH—CH$_2$—), 5.80 (m, —CH$_2$CH=CH$_2$), 5.81 (unresolved m, 14), 6.25 (d, 10), 6.32 (s, 7), 6.32 (s, 8), 6.36 (d, 12), 6.98 (dd, 11). Analysis. Calculated for C$_{24}$H$_{32}$O$_3$: C, 78.22; H, 8.75. Found: C, 78.04; H, 8.78.

From one such experiment, 288 mg (HPLC, 99.4%) of recrystallized methyl 4-oxo-3-(2-propenyl)retinoate was obtained from 1.092 g of methyl 4-oxo-RA. Trituration of the filtrate residue with pentane afforded 179 mg (HPLC, 99.6%); total yield, 38%.

EXAMPLE 8

Methyl 4-Oxo-3-(2-propynyl)retinoate (Compound IV; R=CH$_3$, R$^1$=CH≡CCH$_2$-, R$^2$=H)

This compound was prepared, according to the general procedure described in Example 1, from methyl 4-oxo-RA (1.51 g, 4.6 mmol) and 2-propynyl bromide (820 mg, 6.9 mmol). The crude product was purified by flash chromatography on a column of silica gel with pentane-ethyl acetate as the eluting solvent. Fractions containing methyl 4-oxo-3-(2-propynyl)retinoate (determined by TLC) were combined and concentrated under reduced pressure to a yellow solid (0.81 g) that was recrystallized from ether-pentane: yield, 536 mg (32%); m.p. 117°-119° C.; MS peaks at m/z 366 (M), 351 (M-CH$_3$), 334 (M-CH$_3$OH), 391 (M-CH$_3$OH-CH$_3$), 307 (M—COOCH$_3$); HPLC, 98.5-100% (85:15 acetonitrile-1% aqueous ammonium acetate); UV$_{max}$ 362 nm ($\epsilon$ 53 400), 286 nm ($\epsilon$ 12 900), 231 nm ($\epsilon$ 8000); $^1$H NMR $\delta$ 1.19 (s, 17e), 1.27 (s, 16a), 1.81 and 2.07 (ABM spin system, 2a and 2e), 1.86 (s, 18), 1.98 (t, CH≡C—), 2.03 (d, 19), 2.32 and 2.82 (both m, CH$_2$ of CH≡CCH$_2$—), 2.36 (d, 20), 2.66 (m, 3a), 3.72 (s, OCH$_3$), 5.82 (unresolved m, 14), 6.26 (d, 10), 6.34 (s, 7), 6.34 (s, 8), 6.36 (d, 2), 6.98 (dd, 11). Analysis. Calculated for C$_{24}$H$_{30}$O$_3$: C, 78.65; H, 8.25. Found: C, 78.42; H, 8.46.

EXAMPLE 9

Methyl 4-Oxo-3-(phenylmethyl)retinoate (Compound IV; R=CH$_3$, R$^1$=C$_6$H$_5$CH$_2$-, R$^2$=H)

Methyl 4-oxo-3-(phenylmethyl)retinoate was prepared, according to the general procedure described in Example 1, from methyl 4-oxo-RA and benzyl bromide and was purified by column chromatography: yield, 313 mg from 390 mg of methyl 4-oxo-RA (63%); HPLC, 97.5%. A specimen was recrystallized from ether-hexane: m.p. 93°-95° C.; MS peaks at m/z 418 (M), 403 (M-CH$_3$), 386 (M-CH$_3$OH), 371 (M-CH$_3$OH-CH$_3$); $^1$H NMR $\delta$ 1.09 (s, 17e), 1.13 (s, 16a), 1.62 and 1.65 (ABM spin system, 2a and 2e), 1.88 (s, 18), 2.02 (d, 19), 2.36 (d, 20), 2.48 and 3.49 (ABM spin system, CH$_2$ of C$_6$H$_5$CH$_2$), 2.73 (m, 3a), 3.72 (s, OCH$_3$), 5.82 (unresolved m, 14), 6.25 (d, 10), 6.32 (s, 8), 6.33 (s, 7), 6.35 (d, 12), 6.98 (dd, 11), 7.17-7.32 (aromatic CH). Analysis. Calculated for C$_{28}$H$_{34}$O$_3$ : C, 80.34; H, 8.19. Found: 80.36; H, 7.95.

EXAMPLE 10

Methyl 3-[(Ethoxycarbonyl)methyl]-4-oxoretinoate (Compound IV; R=CH$_3$,

R$^2$=H)

Methyl 4-oxo-RA was treated with ethyl bromoacetate according to the procedure described in Example 1. The crude product as purified by preparative TLC on silica gel (developing solvent, 9:1 pentane-ethyl acetate: MS peaks at m/z 414 (M), 399 (M-CH$_3$), 368 (M-C$_2$H$_5$OH); HPLC, 99.4% (85:15 acetonitrile-1% aqueous ammonium acetate, isocratic).

EXAMPLE 11

Methyl 3,3-Dimethyl-4-oxoretinoate (Compound IV; R=R$^1$=R$^2$=CH$_3$)

A solution of 962 mg (2.7 mmol) of methyl 3-methyl-4-oxoretinoate in 8 mL of anhydrous THF was added during 10 minutes to a chilled (−78° C.) solution of lithium hexamethyldisilazide (3.2 mmol) prepared from 2 mL of anhydrous THF and 1 molar lithium hexamethyldisilazide in THF. The red mixture was stirred at −78° C. for 30 minutes, and about 0.2 mL of methyl iodide was added. The mixture was stirred at −78° C. for 30 minutes, allowed to warm slowly to room temperature, and stirred overnight. The reaction mixture was concentrated under reduced pressure, a saturated aqueous solution (25 mL) of ammonium chloride was added to the concentrated mixture, the resulting mixture was extracted with three 25-mL portions of ether, the ether extract was dried with magnesium sulfate and filtered, and ether was evaporated from the filtrate under reduced pressure. The residue (0.83 g) was flash-chromatographed on a column of silica gel; the eluting solvents used successively were pentane, 97:3 pentane-ethyl acetate, and 94:6 pentane-ethyl acetate. The eluate portions were combined into three fractions, and the first fraction was recrystallized from ether-pentane: weight, 289 mg; HPLC, 94.3% methyl 3,3-dimethyl-4-oxoretinoate. Recrystallization of this material from ether-pentane furnished methyl 3,3-dimethyl-4-oxoretinoate that assayed 98.8% by HPLC (85:15 acetonitrile-1% aqueous ammonium acetate): mp 101°-102° C.; MS peaks at m/z 356 (M), 341 (M-CH$_3$), 324 (M-CH$_3$OH), 309 (M-CH$_3$-CH$_3$OH), 297 (M-COOCH$_3$); UV$_{max}$ 361 nm ($\epsilon$ 51 700), 286 nm ($\epsilon$ 12 300), 230 nm ($\epsilon$ 8000); $^1$H NMR $\delta$ 1.18 (s, 2 CH$_3$ groups at position 3), 1.22 (s, 17e and 16a) 1.78 (s, 2a and 2e), 1.88 (s, 18), 2.03 (d, 19), 2.36 (d, 20), 3.72 (s, OCH$_3$), 5.82 (unresolved m, 14), 6.25 (d, 10), 6.35 (s, 7), 6.35 (s, 8), 6.36 (d, 12), 6.99 (dd, 11). Analysis. Calculated for C$_{23}$H$_{32}$O$_3$: C, 77.48; H, 9.05. Found: C, 77.50; H, 9.07.

HPLC analyses of the second and third fractions from the chromatographic column indicated that they contained 2% and 52%, respectively, of methyl 3,3-dimethyl-4-oxoretinoate.

EXAMPLE 12

Methyl 3.3-Dipropynyl-4-oxoretinoate (Compound IV: R = CH$_3$, R$^1$ = R$^2$ = CH≡CCH$_2$—)

Methyl 3-propynyl-4-oxoretinoate in THF was treated with 1.5 equivalents of propynyl bromide in toluene according to the procedure described in Example 1, but the reaction mixture was not stirred overnight at room temperature. The crude product, which was shown by TLC to contain both the starting material and the desired dipropynyl derivative, was purified by preparative TLC on silica gel (developing solvents successively: pentane, 90% pentane-ethyl acetate, 1:1 pentane-ethyl acetate, and ethyl acetate). The dipropynyl derivative was extracted from the middle band, and additional dipropynyl derivative was obtained in the same way by TLC of the material extracted from the leading band of the first preparative TLC plate; HPLC of both specimens, 96-97%. A specimen was purified further by crystallization from ether-pentane: UV$_{max}$ at 362 nm ($\epsilon$ 52 500), 288 nm $\epsilon$ 15 500), 230-220 nm ($\epsilon$ 11 500); HPLC, 99.2% (85:15 acetonitrile-1% aqueous ammonium acetafe, isocratic); $^1$H NMR $\delta$ 1.27 (s, 16a and 17e), 1.90 (s, 18), 2.03 (d, 19), 2.05 (t, CH of propynyl), 2.15 (s, 2a and 2e), 2.36 (d, 20), 2.54 (m, CH$_2$ of propynyl), 2.60 (m, CH$_2$ of propynyl), 3.72 (s, OCH$_3$), 5.82 (unresolved m, 14), 6.27 (d, 10), 6.33 (A part of AB spin system, 8), 6.36 (d, 12), 6.38 (B part of AB spin system, 7), 6.98 (dd, 11).

EXAMPLE 13

Methyl 3-Cinnamyl-3-methyl-4-oxoretinoate (Compound IV; R = R$^1$ = CH$_3$, R$^2$ = C$_6$H$_5$CH=CHCH$_2$—)

Methyl 3-methyl-4-oxo-RA was treated with 1.2 equivalents of lithium hexamethyldisilazide and 2 equivalents of cinnamyl bromide in anhydrous THF according to the procedure described in Example 1. After the temperature of the reaction mixture had been allowed to rise to room temperature during 1 hour, additional lithium hexamethyldisilazide (ca. 1 equivalent) was added. The mixture was cooled to $-78°$ C., stirred for 30 minutes, allowed to warm to room temperature, and stirred overnight. The crude product was obtained, as usual, by the addition of saturated ammonium chloride solution and extraction with ether and was purified by the use successively of TLC, flash chromatography, and preparative HPLC: UV$_{max}$ at 361 nm ($\epsilon$ 50 700), 292 (sh), 285 ($\epsilon$ 14 400), 252 nm ($\epsilon$ 23 600); $^1$H NMR $\delta$ 1.21 (s, CH$_3$ at position 3), 1.22 (s, 17e), 1.24 (s, 16a), 1.68 and 1.95 (ABM spin system, 2a and 2e), 1.90 (s, 18), 2.03 (d, 19), 2.36 (d, 20), 2.42 and 2.49 (m, CH$_2$ of cinnamyl), 3.72 (s, OCH$_3$), 5.82 (unresolved m, 14), 6.16 (ABM$_2$ spin system, CH of =CHCH$_2$ of cinnamyl), 6.39 (ABM$_2$ spin system, CH of C$_6$H$_5$CH= of cinnamyl), 6.25 (d, 10), 6.35 (s, 7 and 8), 6.35 (d, 12), 6.98 (dd, 11), 7.12-7.38 (m, aromatic CH). Analysis. Calculated for C$_{31}$H$_{38}$O$_3$: C, 81.18; H, 8.35. Found: C, 81.13; H, 8.40.

EXAMPLE 14

Methyl 13-Cis-4-oxoretinoate (Compound VI: R = CH$_3$, R$^1$ = R$^2$ = H)

A mixture of methyl 13-cis-RA (Structure IIb) (473 mg), 64 mL of petroleum ether, and 5.66 g of manganese dioxide was stirred vigorously at room temperature overnight. The mixture was filtered, the filtrate was stirred with a fresh portion (4.7 g) of manganese dioxide for 5 hours, and this mixture was filtered. Both residues of manganese dioxide were washed repeatedly with methanol until TLC indicated that all of the absorbed product had been extracted. The methanol washings were concentrated to dryness in vacuo; weight of residue, 400 mg. The crude product was chromatographed on a column of alumina deactivated with water (10%). Elution of the column with pentane-ether (9:1) afforded 240 mg of methyl 13-cis-4-oxoretinoate that contained minor impurities. This material could be purified further by preparative TLC (developing solvent, 9:1 pentane-ethyl acetate: FAB MS, m/z 329 (M + H), 313 (M-CH$_3$), 297 (M-OCH$_3$); $^1$H NMR $\delta$ 1.19 (s, 16 and 17), 1.85 (s, 18), 1.86 (t, 2), 2.02 (d, 19), 2.08 (d, 20), 2.51 (t, 3), 3.71 (s, OCH$_3$), 5.69 (unresolved m, 14), 6.33 (s, 8), 6.34 (s, 7), 6.36 (m, 10), 6.96 (dd, 11), 7.84 (d, 12).

EXAMPLE 15

Methyl 13-Cis-3-methyl-4-oxoretinoate (Compound VI; R = R$^1$ = CH$_3$, R$^2$ = H)

A solution of methyl 13-cis-4-oxoretinoate (130 mg) in 1.3 mL of anhydrous THF was added during 5 minutes to a solution, maintained at $-78°$ C., composed of 0.65 mL of anhydrous THF and 0.46 mL of a 1 molar solution of lithium hexamethyldisilazide in THF. Then, a solution of 0.38 mL of 1:3 methyl iodideanhydrous toluene was added to the stirred, cold mixture. The resulting reaction mixture was stirred at $-78°$ C. for 1.5 hours and then allowed to warm slowly to room temperature. The mixture was concentrated in vacuo to remove excess methyl iodide; a saturated aqueous solution of ammonium chloride was added; the resulting mixture was extracted with ethyl acetate; and the extract was dried (MgSO$_4$), filtered, and concentrated in vacuo. The residue was purified by preparative TLC on silica gel (developing solvent, 9:1 pentane-ethyl acetate). The product-containing band was leached with ethyl acetate, and the ethyl acetate filtrate was evaporated to dryness. The residue was triturated with petroleum ether, collected by filtration, and dried in vacuo: mp 85°-87° C.; HPLC, 98°99% (85:15 acetonitrile-1% aqueous ammonium acetate); MS peaks at m/z 342 (M), 327 M-CH$_3$), 295 (M-CH$_3$-CH$_3$OH), 283 (M-COOCH$_3$); UV$_{max}$ 363 nm ($\epsilon$ 47 700) 285 nm ($\epsilon$ 13 500), 231 ($\epsilon$ 9400); $^1$H NMR $\delta$ 1.14 (s, 17e), 1.15 (d, 3-CH$_3$,),1.25 (s, 16a), 1.72 and 1.76 (ABM spin system, 2a and 2e), 1.85 (s, 18), 2.02 (s, 19), 2.08 (d, 20), 2.55 (m, 3a), 3.71 (s, OCH$_3$), 5.69 (unresolved m, 14), 6.32 (s, 8), 6.33 (s, 7) 6.36 (m, 10), 6.96 (dd, 11), 7.83 (d, 12). Analysis. Calculated for C$_{22}$H$_{30}$O$_3$·¼H$_2$O: C, 76.15; H, 8.86. Found: C, 76.14; H, 8.83.

EXAMPLE 16

3-Substituted and 3,3-Disubstituted 4-Oxoretinoic Acids (Structures V and VII). General Procedure 3-Substituted-4-oxoretinoic acid esters and 3,3-disubstituted-4-oxoretinoic acid esters represented by Structures IV and VI are hydrolyzed in basic solutions to the corresponding 4-oxoretinoic acids (Structures V and VII) as illustrated by the following general procedure. A solution of the ester in 90% ethanol and containing sodium hydroxide or potassium hydroxide (1.2 mol of base per mol of ester) is heated at 60° C. for about 1 hour under an atmosphere of argon or nitrogen. (The course of the hydrolysis may be monitored by TLC.) The reaction mixture is cooled to room temperature and then extracted with hexane, pentane, or ether to remove any neutral material. The aqueous layer is then acidified to about pH 3, and the resulting mixture is extracted with ethyl acetate or ether. The organic extract is dried (e.g., $MgSO_4$), filtered, and concentrated in vacuo to a solid residue. The residue is purified by recrystallization from an organic solvent or by acidification of a basic solution.

EXAMPLE 17

3-Methyl-4-oxoretinoic Acid (Compound V; R =CH:, $R^2$=H)

The crude product, obtained according to the general procedure (Example 16), was recrystallized from ethyl acetate: mp 210°-211° C.; HPLC, 100% (85:15 acetonitrile-1% aqueous ammonium acetate); MS peaks at m/z 328 (M), 313 (M-$CH_3$), 295 (M-$CH_3$-$H_2O$); $^1$H NMR δ 1.14 (s,17e), 1.15 (d-3-$CH_3$), 1.24 (s,16a), 1.71 and 1.76 (ABM spin system, 2a and 2e), 1.85 (s, 18), 2.03 (s, 19), 2.37 (s, 20), 2.56 (m, 3a), 5.84 (unresolved m, 14), 6.26 (d, 10), 6.33 (s, 7 and 8), 6.38 (d, 12), 7.03 (dd, 11), 10.9 (broad, COOH). Analysis. Calculated for $C_{21}H_{28}O_3$: C, 76.79; H, 8.59. Found: C, 76.57; H, 8.75.

EXAMPLE 18

3-Ethyl-4Oxoretionoic Acid (Compound V; $R^1$=$C_2H_5$, $R^2$=H)

The crude product, obtained according to the general procedure (Example 16), was recrystallized from ethyl acetate: mp 214°-216° C.; HPLC, 99-100% (85:15 acetonitrile-1% aqueous ammonium acetate); MS peaks at m/z 342 (M), 327 (M-$CH_3$), 309 (M-$CH_3$-$H_2O$); 298, 283; $^1$H NMR δ 0.94 (t, $CH_3$ of 3-ethyl), 1.16 (s,17e), 1.23 (s, 16a), 1.39 (m, $CH_2$ of 3-ethyl), 1.66 and 1.80 (ABM spin system, 2a and 2e), 1.85 (s, 18), 1.97 (m, $CH_2$ of 3-ethyl), 2.03 (s, 19), 2.36 (m, 3a), 2.37 (d, 20), 5.84 (unresolved m, 14), 6.26 (d, 10), 6.34 (s, 7 and 8), 6.38 (d, 12), 7.02 (dd, 11). Analysis. Calculated for $C_{22}H_{30}O_3$: C, 77.15, H, 8.83. Found: C, 77.04; H, 8.86.

EXAMPLE 19

4-Oxo-3-(2-propenyl)retinoic Acid (Compound V; $R^1$=$CH_2$=$CHCH_2$—, $R^2$=H)

The crude product, obtained according to the general procedure (Example 16), was recrystallized from ethyl acetate; mp 195°-196° C.; HPLC, 100% (85:15 acetonitrile-1% aqueous ammonium acetate); MS peaks at m/z 354 (M), 339 (M-$CH_3$), 321 (M-$CH_3$-$H_2O$); $^1$H NMR δ 1.15 (s,17e), 1.23 (s,16a), 1.64 and 1.80 (ABM spin system, 2a and 2e), 1.86 (s, 18), 2.04 (s,19), 2.10 and 2.74 (m, $CH_2$ of propenyl group), 2.37 (d, 20), 2.52 (m,3a), 5.04 and 5.06 (m, $CH_2$ of —CH=$CH_2$ of propenyl group), 5.80 (m, CH of propenyl group), 5.84 (unresolved m, 14), 6.26 (d, 10), 6.34 (s, 7 and 8), 6.38 (d, 12), 7.03 (dd, 11). Analysis. Calculated for $C_{23}H_{30}O_3$: C, 77.92; H, 8.53. Found: C, 77.97; H, 8.58.

EXAMPLE 20

4-Oxo-3-(2-propenyl)retinoic Acid (Compound V; $R^1$=CH≡$CHCH_2$—, $R^2$=H)

The crude product, obtained according to the general procedure (Example 16), was recrystallized from ethyl acetate: mp 211°-213° C.; HPLC, 98.7% (85:15 acetonitrile-1% aqueous ammonium acetate); MS peaks at m/z 352 (M), 337 (M-$CH_3$), 319 (M-$CH_3$-$H_2O$); $^1$H NMR δ 1.19 (s,17e), 1.27 (s,16a), 1.81 and 2.06 (ABM spin system, 2a and 2e), 1.86 (s, 18), 1.98 (t, CH of propynyl), 2.04 (s,19), 2.33 and 2.83 (m, $CH_2$ of propenyl), 2.37 (d, 20), 2.66 (m,3a) 5.85 (unresolved (m,14), 6.27 (d, 10), 6.35 (s, 7 and 8), 6.39 (d, 12), 7.03 (dd, 11). Analysis. Calculated for $C_{23}H_{28}O_3$: C, 78.37; H, 8.01. Found: C, 78.32; H, 8.08.

EXAMPLE 21

4-Oxo-3-(2-propenyl)retinoic Acid (Compound V; $R^1$=$CH_6H_5CH_2$—, $R^2$=H)

The crude product, obtained according to the general procedure (Example 16), was recrystallized twice from ethyl acetate: mp 209°-210° C.; HPLC, 99-100% (85:15 acetonitrile-1% aqueous ammonium acetate); MS peaks at m/z 404 (M), 389 (M-$CH_3$), 371 (M-$CH_3$-$H_2O$; $^1$H NMR δ 1.09 (s,17e), 1.13 (s,16a), 1.61 and 1.65 (ABM spin system, 2a and 2e), 1.88 (s, 18), 2.03 (s, 19), 2.37 (d, 20), 2.48 (m, $CH_2$ of benzyl), 2.74 (m, 3a), 3.49 (m, $CH_2$ of benzyl), 5.84 (unresolved m, 14), 6.26 (d, 10), 6.33 (s, 7 and 8), 6.38 (d, 12), 7.02 (dd, 11), 7.14-7.34 (aromatic CH). Analysis. Calculated for $C_{27}H_{32}O_3$: C, 80.16; H, 7.97. Found: C, 80.63; H, 8.09.

EXAMPLE 22

3-Cinnamyl-4-oxoretinoic Acid (Compound V; $R^1$=$C_6H_5$CH=$CHCH_2$—, $R^2$=H)

The crude product, obtained by a procedure similar to that of Example 16, was recrystallized from ethyl acetate: mp 197°-198° C.; HPLC, 98-99% (85:15 acetonitrile-1% aqueous ammonium acetate); MS peaks at m/z 430 (M), 415 (M-$CH_3$), 397 (M-$CH_3$-$H_2O$), 386, 374; $^1$H NMR δ 1.14 (s, 17e), 1.23 (s, 16a), 1.71 and 1.83 (ABM spin system, 2a and 2e), 1.87 (s, 18), 2.04 (s, 19), 2.31 (m, $CH_2$ of cinnamyl), 2.37 (d, 20), 2.61 (m, 3a), 2.85 (m, $CH_2$ of cinnamyl), 5.84 (unresolved m, 14), 6.21 ($ABM_2$ spin system, CH of =$CHCH_2$— of cinnamyl), 6.25 (d, 10), 6.34 (s, 7 and 8), 6.38 (d, 12), 6.42 ($ABM_2$ spin system, CH of phenyl-CH=), 7.03 (dd, 11), 7.15-7.40 (aromatic CH). Analysis. Calculated for $C_{29}H_{34}O_3$: C, 80.89; H, 7.96. Found: C, 80.82; H, 8.00.

EXAMPLE 23

3,3-Dimethyl-4-Oxoretinoic Acid (Compound V; $R^1$=$R^2$=$CH_3$)

The crude product, obtained by a procedure similar to that described in Example 16, was recrystallized from ethanol-ethyl acetate and then from ethyl acetate: mp 226°-228° C.; HPLC, 100% (acetonitrile-1% aqueous ammonium acetate); MS peaks at m/z 342 (M), 327 (M-$CH_3$), 309 (M-$CH_3$- $H_2O$); $^1$H NMR δ 1.18 (s, 2 $CH_3$ groups at position 3), 1.22 (s, 17e and 16a), 1.79 (s, 2a and 2e), 1.88 (s, 18), 2.04 (d, 19), 2.37 (d, 20), 5.84 (unresolved m, 14), 6.27 (d, 10), 6.36 (s, 7 and 8), 6.38 (d, 12), 7.03 (dd, 11). Analysis. Calculated for $C_{22}H_{30}O_3$: C, 77.15; H, 8.83. Found: C, 77.23; H, 8.84.

EXAMPLE 24

Assay for Induction of Differentiation of Cancer Cells to Normal Cells

Evaluation of the differentiation potential of 4-oxoretinoids was carried out with an embryonal carcinoma cell line, F9. Elevation of plasminogen activator release by F9 cells in the presence of retinoids is a marker for inducing differentiation into parietal endoderm (Strickland and Mahdavi, loc. cit.; Strickland and Sawey, loc. cit.). F9 cells were grown at a density of $1 \times 10^5$ cells/mL in the presence or absence of $10^{-7}$, $10^{-8}$, $10^{-9}$, $10^{-10}$, and $10^{-11}$ or molar retinoids for 4 days. Aliquots (20 μL) of the harvest fluid were mixed with 0.13 μM plasminogen, 0.3 mM H-D-Val-Leu-Lys-p-nitroanilide (a synthetic substrate of plasmin), 0.1% Tween 80, and 25 μg of fibrinogen fragments in a final volume of 0.2 mL of Tris-HCl, pH 7.5. After incubation for 4 hours at 25° C., the generation of p-nitroaniline was measured by absorbance at 405 nm. The average absorbencies from duplicate experiments were plotted (semilog plots) versus concentration (molarity). The $ED_{50}$ values were determined by finding the midpoint between the maximal and minimal absorbance values. Results of this assay are summarized in Table I.

EXAMPLE 25

Hamster Trachea Organ Culture Assay

4-Oxoretinoids were evaluated for their capacity to reverse squamous metaplasia and keratinization in organ cultures of tracheas obtained from vitamin A-deficient hamsters. The methods and procedures were those described by Sporn and co-workers (Clamon et al. and Newton et al., loc. cit.). Results of this assay are summarized in Table II.

EXAMPLE 26

Ornithine Decarboxylase Assay

Assays for the reduction by 4-oxoretinoids of ornithine decarboxylase activity induced by 12-O-tetradecanoylphorbol 13-acetate (TPA) were performed by the procedure of Verma et al., *Cancer Research*, Vol. 38, pages 793-801 (1978). Results of this assay are summarized in Table III.

EXAMPLE 27

Antipapilloma Assay

In this assay, tumors are initiated in mice by applying the carcinogen DMBA to the skin of mice and subsequently applying the promoter TPA. The method is that of Verma et al., *Cancer Research*, Vol. 39, pages 419-425, 1979. Results of this assay are summarized in Table IV.

TABLE I

| Induction of Differentiation of Cancer Cells | |
|---|---|
| Compound | Differentiation of F9 Embryonal Carcinoma Cells $ED_{50}{}^a$, M |
| IV; R = $CH_3$, $R^1$ = $CH_3$, $R^2$ = H<br>Example 2 | $20 \times 10^{-10}$ |
| IV; R = $CH_3$, $R^1$ = CH≡$CCH_2$, $R^2$ = H<br>Example 8 | $15 \times 10^{-10}$ |
| IV; R = $CH_3$, $R^1$ = $R^2$ = $CH_3$<br>Example 11 | $9 \times 10^{-10}$ |
| V; $R^1$ = $CH_3$, $R^2$ = H<br>Example 17 | $9 \times 10^{-10}$ |
| V; $R^1$ = $CH_3CH_2$, $R^2$ = H<br>Example 18 | $50 \times 10^{-10}$ |
| V; $R^1$ = $CH_2$=$CHCH_2$, $R^2$ = H<br>Example 19 | $7 \times 10^{-10}$ |
| V; $R^1$ = CH≡$CCH_2$, $R^2$ = H<br>Example 20 | $6 \times 10^{-10}$ |
| V; $R^1$ = $C_6H_5CH_2$, $R^2$ = H<br>Example 21 | $8 \times 10^{-10}$ |
| V; $R^1$ = $C_6H_5CH$=$CHCH_2$, $R^2$ = H<br>Example 22 | $35 \times 10^{-10}$ |
| V; $R^1$ = $R^2$ = $CH_3$<br>Example 23 | $2.3^b \times 10^{-10}$ |

$^a ED_{50}$ is the molar concentration of the retinoid that causes 50% induction of differentiation of the carcinoma cells as measured by the release of plasminogen activator
$^b$Average of two determinations

TABLE II

| Hamster Trachea Organ Culture Assay | |
|---|---|
| Compound | $ED_{50}$, M |
| IV; R = $CH_3$, $R^1$ = $CH_3$, $R^2$ = H<br>Example 2 | $4 \times 10^{-9}$ |
| IV; R = $CH_3$, $R^1$ = $C_6H_5CH_2$, $R^2$ = H<br>Example 9 | $1.1 \times 10^{-8}$ |
| IV; R = $CH_3$, $R^1$ = $R^2$ = $CH_3$<br>Example 11 | $3 \times 10^{-10}$ |
| V; $R^1$ = $CH_3$, $R^2$ = H<br>Example 17 | $2 \times 10^{-9}$ |
| V; $R^1$ = CH≡$CCH_2$, $R^2$ = H<br>Example 20 | $2 \times 10^{-10}$ |
| V; $R^1$ = $C_6H_5CH_2$, $R^2$ = H<br>Example 21 | $1.1 \times 10^{-8}$ |
| All-trans-N-ethylretinamide* | $1 \times 10^{-9}$ |
| All-trans-N-(2-hydroxyethyl)-retinamide* | $1 \times 10^{-10}$ |
| All-trans-N-(4-hydroxyphenyl)-retinamide (4-HPR)* | $3 \times 10^{-10}$ |
| 13-Cis-N-ethylretinamide* | $3 \times 10^{-10}$ |
| 13-Cis-N-(2-hydroxyethyl)-retinamide* | $3 \times 10^{-10}$ |
| 13-Cis-N-(4-hydroxyphenyl)-retinamide* | $>1 \times 10^{-9}$ |

*The value of $ED_{50}$ is taken from Newton et al. (loc. cit.)

TABLE III

| Ornithine Decarboxylase Assay | | |
|---|---|---|
| | Ornithine Decarboxylase Activity, Nanomoles of Carbon Dioxide Per Milligram of Protein Per Half Hour | |
| Compound | Average % of Control Group | No. of Tests |
| IV; R = $CH_3$, $R^1$ = $CH_3$, $R^2$ = H<br>Example 2 | 33 | 3 |
| IV; R = $CH_3$, $R^1$ = $C_6H_5CH$=$CHCH_2$, $R^2$ = H<br>Example 3 | 31 | 2 |
| IV; R = $CH_3$, $R^1$ = $CH_3CH_2$, $R^2$ = H<br>Example 4 | 31 | 3 |
| IV; R = $CH_3$, $R^1$ = $CH_2$=$CHCH_2$, $R^2$ = H<br>Example 7 | 56 | 2 |
| IV; R = $CH_3$, $R^1$ = CH≡$CCH_2$, $R^2$ = H<br>Example 8 | 35 | 2 |
| IV; R = $CH_3$, $R^1$ = $C_6H_5CH_2$, | 77 | 2 |

TABLE III-continued

Ornithine Decarboxylase Assay

| Compound | Ornithine Decarboxylase Activity Nanomoles of Carbon Dioxide Per Milligram of Protein Per Half Hour Average % of Control Group | No. of Tests |
|---|---|---|
| $R^2 = H$ Example 9 | | |
| IV; $R = CH_3$, $R^1 = R^2 = CH_3$ Example 11 | 22 | 3 |
| V; $R^1 = CH_3$, $R^2 = H$ Example 17 | 33 | 3 |
| V; $R^1 = CH_3CH_2$, $R^2 = H$ Example 18 | 40 | 3 |
| V; $R^1 = CH_2=CHCH_2$, $R^2 = H$ Example 19 | 68 | 2 |
| V; $R^1 = CH\equiv CCH_2$, $R^2 = H$ Example 20 | 47 | 2 |
| V; $R^1 = C_6H_5CH_2$, $R^2 = H$ Example 21 | 42 | 4 |
| V; $R^1 = C_6H_5CH=CHCH_2$, $R^2 = H$ Example 22 | 23 | 3 |
| V; $R^1 = R^2 = CH_3$ Example 23 | 26 | 3 |

TABLE IV

Mouse Antipapilloma Assay

| Compound | Average Number of Skin Papillomas/Mouse as % of No. of Papillomas/Mouse in the DMBA-TPA Control Group of Mice |
|---|---|
| IV; $R = CH_3$, $R^1 = CH_3$, $R^2 = H$ Example 2 | 27 |
| IV; $R = CH_3$, $R^1 = CH_3CH_2$, $R^2 = H$ Example 4 | 83 |
| IV; $R = CH_3$, $R^1 = CH_2=CHCH_2$, $R^2 = H$ Example 7 | 42 |
| IV; $R = CH_3$, $R^1 = CH\equiv CCH_2$, $R^2 = H$ Example 8 | 40 |
| IV; $R = R^1 = R^2 = CH_3$ Example 11 | 27 |
| V; $R^1 = CH_3$, $R^2 = H$ Example 17 | 32 |
| V; $R^1 = CH_3CH_2$, $R^2 = H$ Example 18 | 57 |
| V; $R^1 = CH_2=CHCH_2$, $R^2 = H$ Example 19 | 47 |
| V; $R^1 = CH\equiv CCH_2$, $R^2 = H$ Example 20 | 64 |
| V; $R^1 = C_6H_5CH=CHCH_2$ Example 22 | 39 |
| V; $R^1 = R^2 = CH_3$ Example 23 | 27 |

What is claimed is:

1. A compound selected from the group consisting of those that have the structures

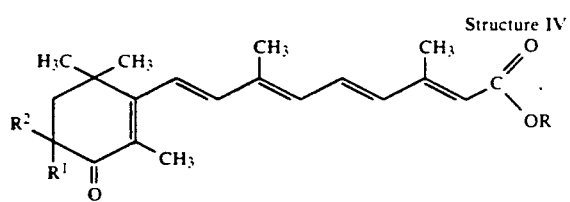

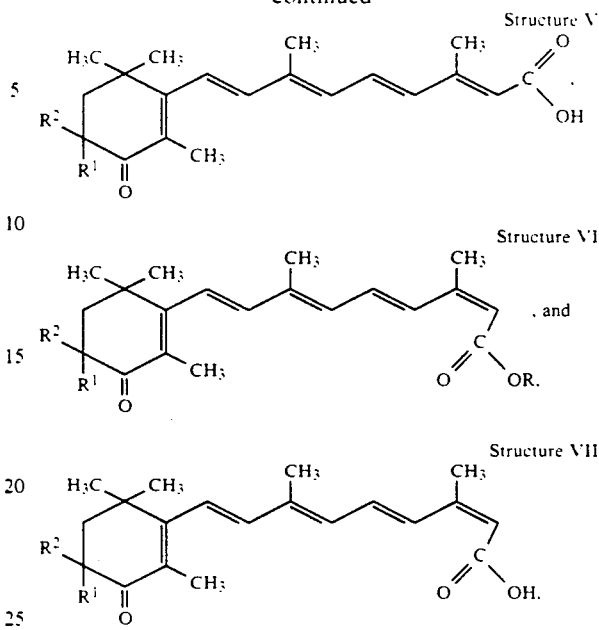

wherein R is a lower alkyl group or an aryl group, and $R^1$ and $R^2$ are the same or different substituents selected from the group consisting of hydrogen, an alkyl group, and aralkyl group, and alkenyl group, an aralkenyl or aralkynyl group, an alkynyl group, and a carboxyalkyl group, provided that $R^1$ and $R^2$ are not both hydrogen.

2. A compound as defined in claim 1 of Structure IV wherein R is $CH_3$, $R^1$ is $CH_3$ and $R^2$ is H.

3. A compound as defined in claim 1 of Structure IV wherein R is $CH_3$, $R^1$ is $CH\equiv CCH_2$, and $R^2$ is H.

4. A compound as defined in claim 1 of Structure IV wherein R, $R^1$ and $R^2$ are each $CH_3$.

5. A compound as defined in claim 1 of Structure V wherein $R^1$ is $CH_3$ and $R^2$ is H.

6. A compound as defined in claim 1 of Structure V wherein $R^1$ is $CH_3CH_2$, and $R^2$ is H.

7. A compound as defined in claim 1 of Structure V wherein $R^1$ is $CH_2=CHCH_2$ and $R^2$ is H.

8. A compound as defined in claim 1 of Structure V wherein $R^1$ is $CH\equiv CCH_2$ and $R^2$ is H.

9. A compound as defined in claim 1 of Structure V wherein $R^1$ is $C_6H_5CH_2$ and $R^2$ is H.

10. A compound as defined in claim 1 of Structure V wherein $R^1$ is $C_6H_5CH=CHCH_2$ and $R^2$ is H.

11. A compound as defined in claim 1 of Structure V wherein $R^1$ and $R^2$ are each $CH_3$.

12. A compound as defined in claim 1 of Structure IV wherein R is $CH_3$, $R^1$ is $CH_6H_5CH_2$ and $R^2$ is H.

13. A compound as defined in claim 1 of Structure IV wherein R is $CH_3$, $R^1$ is $C_6H_5CH=CHCH_2$ and $R^2$ is H.

14. A compound as defined in claim 1 of Structure IV wherein R is $CH_3$, $R^1$ is $CH_3CH_2$ and $R^2$ is H.

15. A compound as defined in claim 1 of Structure IV wherein R is $CH_3$, $R^1$ is $CH_2=CHCH_2$ and $R^2$ is H.

16. A compound as defined in claim 1 of Structure IV wherein R is $CH_3$, $R^1$ is $CH_3H_7$, and $R^2$ is H.

17. A compound as defined in claim 1 of Structure IV wherein R is $CH_3$, $R^1$ is $CH_4H_9$, and $R^2$ is H.

18. A compound as defined in claim 1 of Structure IV wherein R is $CH_3$.

$R^1$ is
$C_2H_5OCCH_2—$,
‖
O and $R^2$ is H.

19. A compound as defined in claim 1 of Structure IV wherein R is $CH_3$, $R^1$ and $R^2$ are both $CH\equiv CCH_2$.

20. A compound as defined in claim 1 of Structure IV wherein R and $R^1$ are both $CH_3$ and $R^2$ is $C_6H_5CH=CHCH_2$.

21. A compound as defined in claim 1 of Structure VI wherein R and $R^1$ are both $CH_3$, and $R^2$ is H.

22. A method for treatment for the prevention of cancer, for the treatment of pre-malignant conditions, or for the treatment of established cancers comprising administering to an individual in need of such treatment a therapeutically effective amount of a compound as defined in claim 1.

23. A pharmaceutical composition comprising a compound of claim 1 or a pharmaceutically acceptable salt thereof together with a pharmaceutically acceptable carrier for oral, topical or parenteral administration to a mammal.

24. A method of inducing differentiation in a cancer cell comprising
contacting the cancer cell with differentiation-inducing effective amount of a compound of claim 1.

* * * * *

UNITED STATES PATENT AND TRADEMARK OFFICE
CERTIFICATE OF CORRECTION

PATENT NO.   : 5,124,083
DATED        : June 23, 1992
INVENTOR(S)  : Y. Fulmer Shealy It is certified that error appears in the above-identified patent and that said Letters Patent is hereby corrected as shown below:

In column 1, between the title and the heading "BACKGROUND OF THE INVENTION", insert the following:
-- This invention was made with Government support under Grant No. P01-CA-34968, awarded by the Department of Health and Human Services. The Government has certain rights in the invention. --

Signed and Sealed this

Seventeenth Day of August, 1993

Attest:

BRUCE LEHMAN

*Attesting Officer*        *Commissioner of Patents and Trademarks*